United States Patent [19]
O'Rourke et al.

[11] 4,386,066
[45] May 31, 1983

[54] IMMUNOGENIC COMPLEX FROM N. GONORRHOEAE

[75] Inventors: Edward C. O'Rourke, West Point, Pa.; W. Wardle Fullerton, La Mesa, Calif.

[73] Assignee: Merck & Co., Inc., Rahway, N.J.

[21] Appl. No.: 294,855

[22] Filed: Aug. 20, 1981

[51] Int. Cl.$^3$ .................. A61K 39/095; C12P 21/00; C12N 1/20
[52] U.S. Cl. ........................ 424/92; 424/88; 435/253; 435/68
[58] Field of Search .................. 424/92, 177, 180; 536/1; 435/68, 253

[56] References Cited

U.S. PATENT DOCUMENTS 4,203,971  5/1980  Buchanan ........................ 424/92
4,220,638  9/1980  Karkhanis et al. ............... 424/92

OTHER PUBLICATIONS

Johnston et al., *Intl. Symp. Gonorrhea*, Ottawa, Canada, (1973).
Hill et al., *Inf. And. Imm.* 10, 605, (1974).
Frasch et al., *J. Exp. Med.*, 147, 629 (1978).

*Primary Examiner*—Blondel Hazel
*Attorney, Agent, or Firm*—Gabriel Lopez; Frank M. Mahon; Hesna J. Pfeiffer

[57] ABSTRACT

A vesicular, immunogenic, non-pyrogenic complex is obtained from isolates of *N. gonorrhoeae* by cultivating *N. gonorrhoeae* on a suitable nutrient medium; harvesting and centrifuging the cells; extracting the cell pellet with TRITON X-100 at alkaline pH; suspending the solids remaining after extraction in aqueous medium and precipitating in the cold with ethanol.

3 Claims, No Drawings

IMMUNOGENIC COMPLEX FROM N. GONORRHOEAE

BACKGROUND OF THE INVENTION

A vesicular, immunogenic, non-pyrogenic complex is obtained from isolates of *N. gonorrhoeae* by cultivating *N. gonorrhoeae* on a suitable nutrient medium; harvesting and centrifuging the cells; extracting the cell pellet with TRITON X-100 at alkaline pH; suspending the solids remaining after extraction in an aqueous medium and precipitating in the cold with ethanol.

The instant invention relates to a novel vesicular, immunogenic, non-pyrogenic complex obtained from isolates of *N. gonorrhoeae*. More particularly, the instant invention relates to said immunogenic complex; to the process for obtaining said immunogenic complex from isolates of *N. gonorrhoeae*; and to compositions for the safe and effective administration of said immunogenic complex to mammalian species in order to provide protection against *N. gonorrhoeae*.

The instant invention is based upon applicant's discovery that a vesicular, immunogenic, non-pyrogenic complex may be obtained from isolates of *N. gonorrhoeae* by cultivating an isolate of *N. gonorrhoeae* on a suitable nutrient medium; harvesting and centrifuging the cells; extracting the cells with TRITON X-100 (polyoxyethylene octyl phenol, a non-ionic detergent) at alkaline pH; suspending the solids remaining after extraction in an aqueous medium and precipitating in the cold with ethanol; and releasing and removing RNA and DNA by nuclease digestion followed by diafiltration to remove the enzymes and degradation products. The material is then dispersed and solubilized by sonication and filtered through a 0.45 $\mu m$ polysulphone membrane. It is contemplated that immunogenically effective amounts of the complex of this invention in suitable formulations will be administered as a vaccine against *N. gonorrhoeae* infection.

Procedures for cultivating isolates of *N. gonorrhoeae* and for producing the immunogenic complex of this invention therefrom are described in detail below.

FERMENTATION OF N. GONORRHOEAE

A. Preparation of Inoculum For Fermentation

1. Swab GCIV agar plates (23) with *N. gonorrhoeae* stock culture.

2. Incubate plates for about 17 hours in an 8% $CO_2$ water saturated $CO_2$ incubator.

3. Harvest the cells from the surface of the plates; pool the collected cells and transfer to 700 ml of fermentation broth in a 1000 ml nephelometer flask. The fermentation broth consists of Mueller-Hinton broth (DIFCO) containing, per 1000 ml final volume, 30 ml of 7.5% aqueous $NaHCO_3$ and 11 ml of IsoVitalex (Baltimore Biological Laboratories, Baltimore, Md.).

4. Remove 350 ml from the flask and transfer to a second 1000 ml nephelometer flask.

5. Place both flasks in a shaker water bath at 37° C. with 160–200 oscillations per minute (½ inch stroke).

6. Monitor growth by measuring optical density at 15 minute intervals. Stop the incubation when the optical density is 0.2 to 0.4.

B. 7-Liter Fermentation

Add the pooled contents from the shake flasks obtained above to 7 liters of fermentation broth (the broth is the same as that used in preparing the inoculum). Ferment at 37° C. with stirring at 450 rpm while passing air (2.9 liter/min.) and $CO_2$ (0.6 liters/min.) through the medium. Continue fermentation for about 5 hours or until the bacteria reach their stationary phase of growth. Inactivate the bacteria by adding thimerosol (final concentration 1/5000) and store overnight at 5° C. with gentle mixing. Transfer the broth immediately into 500 ml centrifuge tubes. Centrifuge at 5000×g for 20 minutes at 2° C.

Although the fermentation technique described above is the preferred means for cultivating the *N. gonorrhoeae* used in preparing the immunogenic complex of this invention, it will be obvious that the *N. gonorrhoeae* also can be obtained by agar growth. Thus, for example, uncontaminated GCIV agar plates may be streaked with *N. gonorrhoeae* seed culture and incubated at 37° C. for 16–18 hours. The harvested cells from such plates then may be used in the preparation of the immunogenic complex of this invention.

The immunogenic complex of this invention is prepared by the techniques described below. All procedures are conducted with aseptic techniques.

PREPARATION OF IMMUNOGENIC COMPLEX

A. Preparation of 5000×g Pellet (Done at 2°–8° C.)

At the end of the fermentation described above, fill 12 gas sterilized 500 ml centrifuge bottles having sealing caps with fermentation broth and centrifuge at 5000×g at 2° C. for 20 minutes. Decant the supernatants. Pool the pellets by scraping into two 500 ml centrifuge bottles having sealing caps. Resuspend the pellets by mixing while gradually adding 400 ml of physiological saline to each centrifuge bottle. Store the GC material at −70° C. until needed. Thaw and centrifuge at 5000×g for 20 minutes. Decant the supernatant to obtain saline washed 5000×g pellets.

B. Treatment With Triton X-100 (Done At Room Temperature Except Where Noted)

Prepare on the same day the following solution. Add 17.5 ml of TRITON X-100 (non-ionic detergent, polyoxyethylene oxtyl phenol, Rohm & Haas Co., Philadelphia, Penna.) to about 320 ml of sterile pyrogen-free deionized water with stirring. Add 1.75 ml 2 molar tris(hydroxymethyl)-aminomethane and 3.5 ml 1 molar $MgCl_2$. When the TRITON X-100 is completely dissolved, adjust the pH to 8.5 with 1 normal HCl. Adjust the final volume to 350 ml with additional deionized water and filter through a 0.2 $\mu m$ membrane filter to sterilize.

Transfer the 5000×g pellets obtained above to a beaker. Rinse the centrifuge bottles with small volumes of TRITON X-100 solution and transfer to the beaker. Mix the 5000×g pellets with the solution to form a thick paste, then gradually add a total of 300 ml of TRITON X-100 solution. Stir rapidly for 30 minutes. Avoid foaming. Transfer about 40 ml of the resulting mixture to each of 8 screw-cap polycarbonate centrifuge tubes and centrifuge at 48,000×g for 20 minutes at 2°–8° C. Decant the supernatant.

C. Treatment with Ethanol (Done At Room Temperature Except Where Noted)

Add 2 ml of physiological saline to each tube and dislodge the pellets. Pour the pellets into a 15 ml dounce-type tissue grinder and homogenize briefly to resuspend. Transfer the homogenate to a 1000 ml flask. Rinse the tissue grinder with physiological saline and add the rinses to the flask. Adjust final volume to 100 ml with physiological saline and add 400 ml of absolute ethanol at −20° C. mixing well. Place flask at −20° C. overnight.

Shake the flask well to suspend evenly the precipitate. Collect the ethanol precipitate by centrifugation in 150 ml bottles at 2500×g for 20 minutes at 2°–8° C. Decant the supernatant. Break up the pellets while adding cold 80% ethanol (at least 100 ml per bottle). When a fine, homogenous suspension is obtained, centrifuge at 2500×g for 20 minutes at 2°–8° C. Decant the supernatant.

D. Nuclease Treatment and XM-300 Diafiltration (Done At Room Temperature)

Suspend the washed ethanol precipitate pellets obtained above in 20 ml phosphate buffer (0.062 molar sodium phosphate, pH 7.0) containing 0.02 mole of $MgCl_2$ using a dounce-type tissue grinder or a glass stirring rod. Prepare the nuclease treatment reaction mixture so as to contain about 3.5 mg/ml protein (Lowry) as follows.

| | |
|---|---|
| 16.6 ml | Suspended Ethanol (8.73 mg/ml) Precipitate Pellet |
| 22.0 ml | Phosphate Buffer with $MgCl_2$ |
| 1.7 ml | DNase (1 mg/ml) (Sterile) |
| 1.7 ml | RNase (1 mg/ml) (Sterile) |

Incubate at room temperature for 1 hour with frequent gentle stirring in a 100 ml beaker.

After incubation, load the reaction mixture directly into a sterile thin channel ultrafiltration cell fitted with an AMICON XM-300 membrane (Amicon Corporation, Lexington, Mass.). Dilute the reaction mixture to 400 ml with phosphate buffer. Begin running the unit in the diafiltration mode using phosphate buffer at 10 psi (pounds per in$^2$) and the highest pump speed compatible with this pressure. Run, collecting at least 7 diavolumes of ultrafiltrate. Change to sterile pyrogen-free deionized water. Increase the pressure to 20 psi with increased pump speed. Run, collecting at least 7 diavolumes of ultrafiltrate. Stop diafiltration and change to concentration mode. Concentrate at 20 psi to 50 ml. Remove the sample and rinse the cell with 25 ml of the deionized water. Pool the sample and rinses to obtain 107 ml of XM-300 retentate (1.18 mg/ml Lowry protein). Store the retenate at 2°–8° C.

E. Probe Sonication And Filtration (Done At Room Temperature Except Where Noted)

Add 2 ml of the retentate obtained above to 2 gm of acid washed glass beads (0.1 to 0.11 mm diameter) in a 16×125 mm tube. Sonicate using a standard microtip at an output setting of 7 (about 32 watts) for 15 minutes with the tube immersed in an ice-water bath. Add 2 ml of cold deionized water to the sample and mix well. Pipet off the supernatant and filter through Nalgene 115 ml filter units fitted with a 0.45 μm polysulphone membrane. Rinse the beads twice with 2 ml of the deionized water and filter the supernatants through the same filter unit. Repeat the process until all of the XM-300 retentate is processed to obtain the final product (159 ml, 0.24 mg/ml Lowry protein).

Alternatively, the XM-300 retentate from Step D may be treated by conventional flow sonication techniques or in an ultrasonic cleaner bath at 50–55 KHZ.

The process described above may be summarized as follows:

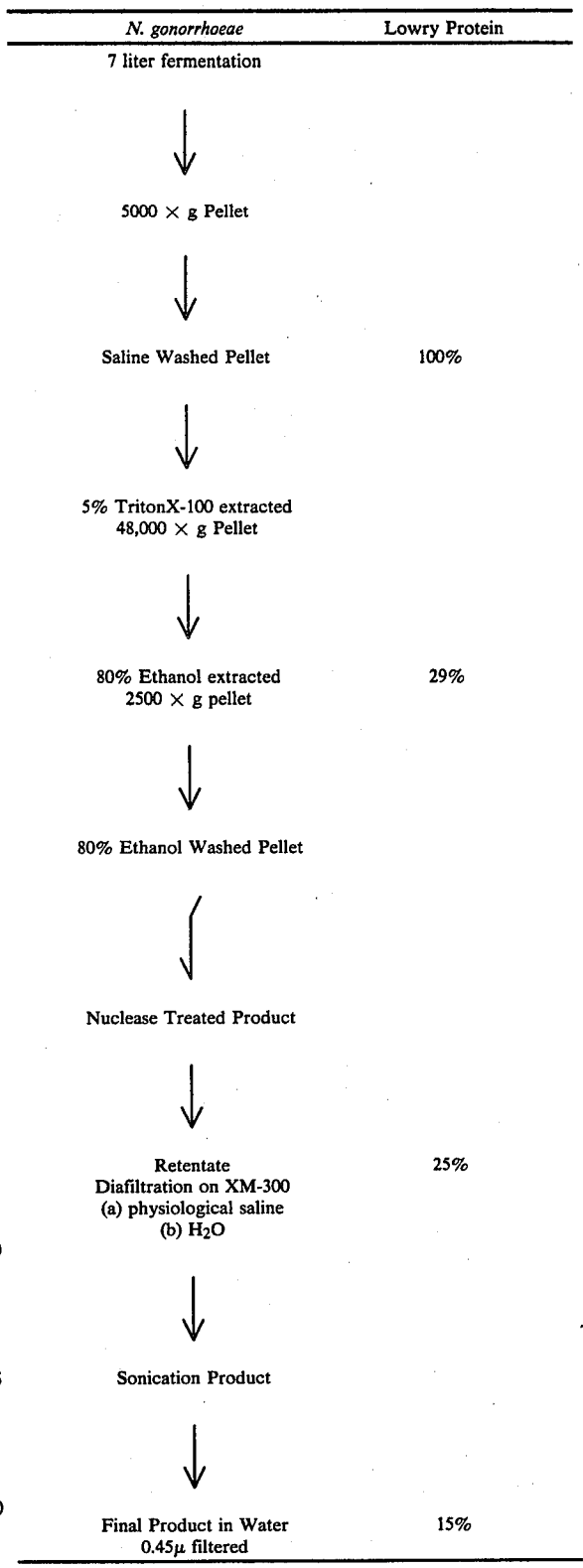

CHEMICAL-PHYSICAL ANALYSIS OF ISOLATED COMPLEX

A. Composition As % of Dry Weight (XM-300 Retentate-Fermentor Grown)

| | |
|---|---|
| Protein (Lowry) | 70–90 |
| Total Carbohydrate (Phenol—H$_2$SO$_4$) | 1.5–5.5 |
| Ketodeoxyoctonate (Thiobarbituric Acid Method) | 0.45–0.55 |
| RNA (Orcinol) | 1.1–1.6 |
| DNA (Diphenylamine) | 0–1.5 |
| Total Lipid (Sulpho-Phospho-Vanillin) | 0.4–3.5 |
| Total Phosphate | 0.4–0.65 |
| Hexosamines | 1.0–3.5 |
| Metals (X-Ray Fluoroescence) | P,S,Si Al and Fe variable |
| TRITON X-100 | <0.04 |

B. SDS-Polyacrylamide Gel Electrophoresis Of Isolated Complex

Vaccine preparations can be characterized and analyzed by sodium dodecyl sulfate-polyacrylamide gel electrophoresis according to the method of Weber and Osborn [J. Biol. Chem. 244:4406(1969)]. With this method at least 27 bands can be readily observed in the isolated complex of this invention. The bands are distributed throughout the length of the gel and their calculated sub-unit molecular weights range from over 150,000 to less than 14,000. In general, the patterns of the bands are similar for material isolated from different strains whether grown on agar or in liquid media. However, variations may be observed: there may be differences in the amount of a particular band present in different preparations; one or two bands may be present in some preparations and not in others; and, a band may show slight differences in molecular weight in different preparations. In all cases, the pattern is dominated by a strongly staining band with a molecular weight in the range 35,000 to 39,000. This band is the subunit polypeptide of the major protein of the outer membrane. Other prominent bands occur with the following approximate weights: 150,000; 115,000; 90,000; 70,000; 45,000; 32,000–22,000, a group of four bands; and 20,000–15,000, a group of 2 to 3 diffuse bands.

ANTIGENICITY OF ISOLATED COMPLEX

The antigenicity of the isolated complex of this invention conveniently may be measured by standard serum bactericidal antibody (SBA) assay employing conventional techniques. Typical results of such assay are shown in the following table:

| SERUM BACTERICIDAL ANTIBODY (SBA) RESPONSES OF GUINEA PIGS To *N. gonorrhoeae* (Strain 340)-Three Doses | | |
|---|---|---|
| Sample | Dose mcg Protein | SBA |
| Starting Material (5000 × g pellet) | 100 | ≧1:640 |
| | 20 | 1:160 |
| Probe Sonicated and filtered | 100 | ≧1:640 |
| | 20 | 1:160 |
| Saline Placebo | — | <1:5 |

OPSONIC ACTIVITY OF ISOLATED COMPLEX

A standarized gonococcal strain is incubated with various heat-inactivated test serum samples. The serum-treated gonococci are injected intravenously into 11-day old chick embryos. The eggs are incubated and subsequently observed for viability. Where specific opsonic antibody activity exists in adequate amounts, the chick embryos are protected from an otherwise lethal challenge of gonococci. Results of a typical assay are as shown in the following table.

| OPSONIC ACTIVITY OF GC (strain 340) FERMENTER GROWN FRACTIONS IN GUINEA PIGS ADMINISTERED INTRAPERITONEALLY THREE TIMES | | | | |
|---|---|---|---|---|
| SAMPLE | FRACTION | PROTEIN (mcg/ml) | BLEEDING | OPSONIN TITER (Chick embryo) |
| 168-2 | Starting Material (5000 × g Pellet) | 100 | Pre Post | 1:127 1:2560 |
| 168-10 | Sonicated-Filtered XM-300 RTT(ETOH) | 100 | Pre Post | 1:180 1:2032 |
| CM-258 | Placebo | — | Pre Post | 1:143 1:90 |

PYROGENICITY OF ISOLATED COMPLEX

The pyrogenicity of the immunogenic complex of this invention conveniently may be measured by the standard rabbit pyrogen test employing conventional techniques. Typical results of the rabbit pyrogen test are shown in the following table.

| RABBIT PYROGEN ASSAY *NEISSERIA GONORRHOEAE* VACCINE (strain Melvin) | | |
|---|---|---|
| SAMPLE | *MPD | Maximum Temp. Rise (°C.) |
| Vaccine Lot 781 | 0.05 | 0.1°, 0.2°, 0.3° |
| | 0.025 | 0.0°, 0.0°, 0.2° |
| Placebo (M-258) (10 ml-1 Kg Body Wt.) | — | 0.1°, 0.6°, 0.1° |

*MPD—Minimum pyrogenic dose-mcg protein/ml/kg rabbit

IMMUNOGENIC ACTIVITY OF ISOLATED COMPLEX

Chimpanzees received five injections (lot 781, strain Melvin, 148 mcg gonococcal protein per injection) on a weekly basis. Nineteen days after the last injection all chimpanzees (including placebo controls) received a live challenge of virulent gonococci intraurethrally. All chimpanzees were bacteriologically cultured. All six vaccinees were free of gonococcal infection while five of six placebo injected chimpanzees were positive for gonococcal infection. Statistically significant immunogenic response was achieved in the vaccinees. These results are summarized in the following table.

| ANTIBODY RESPONSES AND INFECTION PATTERNS OF CHIMPANZEES THAT WERE IMMUNIZED (*NEISSERIA GONORRHOEAE* VACCINE-LOT 781) AND CHALLENGED | | | | |
|---|---|---|---|---|
| Chimp No. | Immunization Status | Serology & Infection Status | Challenge Period-Day 47 | 53 |
| 010 | Vaccinee | *Bactericidal | 1:40 | — |
| | | **Opsonin | 1:1525 | — |
| | | Infection | 0 | 0 |
| 029 | Vaccinee | Bactericidal | 1:40 | — |
| | | Opsonin | 1:904 | — |
| | | Infection | 0 | 0 |
| 055 | Vaccinee | Bactericidal | 1:80 | — |
| | | Opsonin | 1:2560 | — |
| | | Infection | 0 | 0 |

ANTIBODY RESPONSES AND INFECTION PATTERNS OF CHIMPANZEES THAT WERE IMMUNIZED (*NEISSERIA GONORRHOEAE* VACCINE-LOT 781) AND CHALLENGED

| Chimp No. | Immunization Status | Serology & Infection Status | Challenge Period-Day 47 | 53 |
|---|---|---|---|---|
| 056 | Vaccinee | Bactericidal | 1:40 | — |
|  |  | Opsonin | 1:452/1:1662 | — |
|  |  | Infection | 0 | 0 |
| 062 | Vaccinee | Bactericidal | 1:40 | — |
|  |  | Opsonin | 1:411/1:1072 | — |
|  |  | Infection | 0 | 0 |
| 072 | Vaccinee | Bactericidal | 1:40 | — |
|  |  | Opsonin | 1:1436 | — |
|  |  | Infection | 0 | 0 |
| 030 | Placebo | Bactericidal | <1:5 | 0 |
|  |  | Opsonin | <1:320 | — |
|  |  | Infection | 0 | 3+ |
| 034 | Placebo | Bactericidal | <1:5 | — |
|  |  | Opsonin | 1:398 | — |
|  |  | Infection | 0 | ± |
| 035 | Placebo | Bactericidal | <1:5 | — |
|  |  | Opsonin | <1:320 | — |
|  |  | Infection | 0 | 3+ |
| 066 | Placebo | Bactericidal | 1:5 | — |
|  |  | Opsonin | 1:398/1:320 | — |
|  |  | Infection | 0 | 0 |
| 073 | Placebo | Bactericidal | <1:5 | — |
|  |  | Opsonin | 1:356/1:320 | — |
|  |  | Infection | 0 | 4+ |
| 074 | Placebo | Bactericidal | <1:5 | — |
|  |  | Opsonin | 1:356 | — |
|  |  | Infection | 0 | 4+ |

*Bactericidal — a dash indicates no bleeding for that date; all pre-titers (day 0) < 1:2.5.
**Opsonin — when the pre-immunization titer was other than 1:320 varied it is presented above the post-immunization value for that day. A dash indicates no bleeding for that date.
Infection key:
± 50 gonococcal colonies (two urethral cultures)
1+ 51–200 gonococcal colonies (two urethral cultures)
2+ 201–500 gonococcal colonies (two urethral cultures)
3+ 501–750 gonococcal colonies (two urethral cultures)
4+ 750 gonococcal colonies (two urethral cultures)

The immunogenic complex of this invention may be sterilized by filtration and preserved with, for example, thimerosal (0.005%), phenol (0.25%), methyl parabens (0.1%) propyl parabens (0.02%), thiocid (0.01%), phenoxyethanol (0.375%), benzyl alcohol (0.9%), benzanthonium chloride (0.025%), formaldehyde (0.005%) and the like; thimerosal, thiocid, phenoxyethanol and the methyl and propyl parabens being preferred, and may be subdivided into suitable containers for distribution as a vaccine. As a vaccine, it may be administered as an injectable in a suitable physiologically acceptable medium such as, for example, phosphate buffered saline and the like, either alone or in combination with adjuvants wellknown in the art such as, for example, alum which may be employed in an amount sufficient to afford up to 1.25 mg of aluminum by assay per dose.

Typically, in the preparation of vaccines, the immunogenic complex of this invention is moved from the filtration step described above to alum adsorption by adjusting the pH of the suspension (Step E, above) to about pH 7.0 by slowly adding 0.01 N hydrochloric acid. The volume of pre-formed alum required for adsorption may be calculated using the formula:

$$Z = (Y \cdot X/1500)$$

wherein
Y = volume of immunogenic complex (ml)
X = Lowry protein (mcg/ml)
Z = volume of preformed alum (ml)

Slowly add the pre-formed alum (4.55 mg Al+++/ml) and titrate with 0.1 N sodium hydroxide in order to maintain the pH in the 6.2–6.8 range. When all the alum has been added, adjust to a final pH of 6.2. Mix the suspension for three hours at room temperature. Centrifuge at 1500×g for 20 minutes. Resuspend the pellet in sterile, isotonic saline to a final volume of 10×z. Add thimerosal to a final concentration of 1:20,000.

Immunogenic response is achieved in adult humans by injection of 0.25 to 3.0 ml unit doses proportioned so as to deliver from 5 to 500 mcg protein per dose. Typically, 0.5 ml doses containing 50 mcg protein are employed. Two to three unit dose injections over a 1 to 3 month period are employed in order to impart a primary immunogenic response and, desirably, are followed by a booster injection at periods of from 1 to 3 years.

The subject matter which applicants regard as their invention is particularly pointed out and distinctly claimed as follows:

What is claimed is:

1. A method of obtaining a vesicular, antigenic, immunogenic, non-pyrogenic complex obtained from strains of *N. gonorrhoeae* characterized by containing on a dry weight basis about 70–90% protein, about 1.5–5.5% total carbohydrate, about 0.45–0.55% ketodeoxyoctanoate, about 1.1–1.6% RNA, about 0–1.5% DNA, about 0.4–3.5% total lipid, about 0.4–0.65% total phosphate and about 1.0–3.5% hexosamines and being characterized on SDS-polyacrylamide gel electrophoresis by sub-unit bands having molecular weights of about 150,000, 115,000, 90,000, 70,000, 45,000, 39,000–35,000, 32,000–22,000 and 20,000–15,000, which comprises cultivating *N. gonorrhoeae* on a suitable nutrient medium, harvesting and centrifuging the cells at 5000×g at 2°–4° C.; extracting the cell pellet with 5% TRITON X-100 in the presence of tris(hydroxymethyl)amino ethane and magnesium chloride at alkaline pH; suspending the solids remaining after extraction in aqueous medium and precipitating with cold ethanol; suspending the ethanol precipitate in physiological saline and incubating with DNase and RNase; removing nucleases and degraduation products by diafiltration; and purifying by sonication and filtration through a 0.45 μm polysulphone filter.

2. The process of claim 1 wherein the ethanol precipitation is carried out at about −20° C.

3. The process of claim 1 wherein sonication is carried out by probe sonication at 0°–8° C.

* * * * *